(12) United States Patent
He et al.

(10) Patent No.: US 12,349,641 B2
(45) Date of Patent: Jul. 8, 2025

(54) METHOD FOR ORGANICALLY PLANTING DENDROBIUM

(71) Applicant: Southwest Forestry University, Kunming (CN)

(72) Inventors: Xiahong He, Kunming (CN); Rui Shi, Kunming (CN); Shu He, Kunming (CN); Bingjie Xiong, Kunming (CN); Youguo Huang, Kunming (CN); Xingru Yan, Kunming (CN); Ao Zhang, Kunming (CN); Xixi Liang, Kunming (CN)

(73) Assignee: Southwest Forestry University (CN)

( * ) Notice: Subject to any disclaimer, the term of this patent is extended or adjusted under 35 U.S.C. 154(b) by 327 days.

(21) Appl. No.: 17/896,596

(22) Filed: Aug. 26, 2022

(65) Prior Publication Data

US 2023/0210074 A1 Jul. 6, 2023

(30) Foreign Application Priority Data

Dec. 31, 2021 (CN) .......................... 202111660326.3

(51) Int. Cl.

| | | |
|---|---|---|
| *A01H 6/62* | (2018.01) | |
| *A01H 4/00* | (2006.01) | |
| *C12N 1/20* | (2006.01) | |
| *C12R 1/11* | (2006.01) | |
| *C12R 1/12* | (2006.01) | |
| *C12R 1/865* | (2006.01) | |

(52) U.S. Cl.
CPC ............. *A01H 4/008* (2013.01); *A01H 4/001* (2013.01); *A01H 6/62* (2018.05); *C12N 1/205* (2021.05); *C12R 2001/11* (2021.05); *C12R 2001/12* (2021.05); *C12R 2001/865* (2021.05)

(58) Field of Classification Search
CPC .......... A01H 4/008; A01H 6/62; A01H 4/001; C12R 2001/11; C12R 2001/865; C12R 2001/12; C12N 1/205
See application file for complete search history.

(56) References Cited

FOREIGN PATENT DOCUMENTS

| CN | 105503297 A | | 4/2016 |
|---|---|---|---|
| CN | 109329016 A | * | 2/2019 |
| CN | 109511535 A | | 3/2019 |
| CN | 109845632 A | * | 6/2019 |
| CN | 110024654 A | | 7/2019 |
| CN | 110199739 A | | 9/2019 |
| CN | 112189555 A | | 1/2021 |

OTHER PUBLICATIONS

Shrestha, A. K., Dahal, N. R., & Ndungutse, V. (2010). Bacillus Fermentation of Soybean: A Review. Journal of Food Science and Technology Nepal, 6, 1-9. (Year: 2010).*
El-Sherif, A. G., El-kady, H. A., Gad, S. B., & Shalaby, M. M. (2018). Impact of Bio-Fertilizer EM and Plants Dried Leaf Powders of Water Hyacinth or Turmeric on Tomato Plants Infected by Meloidogyne incognita at Greenhouse Conditions. Journal of Plant Protection and Pathology, 9(2), 77-82. (Year: 2018).*
Search Report for Application No. GB2212509.0 dated Feb. 21, 2023. 1 pg.
Search Report dated Oct. 19, 2022 from Office Action for Chinese Application No. 202111660326.3 issued Oct. 26, 2022. 1 pg.

* cited by examiner

*Primary Examiner* — Amjad Abraham
*Assistant Examiner* — Dequantarius Javon Speed
(74) *Attorney, Agent, or Firm* — Lerner David LLP

(57) ABSTRACT

A method for organically planting *Dendrobium*, including using a planting medium in the epiphytic planting step of *Dendrobium*. The raw materials of planting medium include fermented powder of *Dendrobium candidum* leaves and sawdust; a method for preparing the fermented powder of *Dendrobium candidum* leaves is as follows: cutting *Dendrobium candidum* leaves into small pieces and mashing the small pieces of *Dendrobium candidum* leaves to obtain materials to be fermented, and then adding liquid medium to the materials to be fermented to obtain fermentation system; sterilizing the fermentation system, adding fermentation bacteria to the fermentation system to obtain a mixture, fermenting and filtering the mixture to obtain post-culturing fermentation broth and fermented products of *Dendrobium candidum* leaves, dewatering and crushing the fermented products of *Dendrobium candidum* leaves to obtain fermented powder of *Dendrobium candidum* leaves.

9 Claims, No Drawings

METHOD FOR ORGANICALLY PLANTING DENDROBIUM

CROSS REFERENCE TO RELATED APPLICATION

This patent application claims the benefit and priority of Chinese Patent Application No. 202111660326.3, entitled "Method for organically planting *Dendrobium*" filed on Dec. 31, 2021, the disclosure of which is incorporated by reference herein in its entirety as part of the present application.

TECHNICAL FIELD

The present disclosure relates to the technical field of *Dendrobium* planting, in particular to a method for organically planting *Dendrobium*.

BACKGROUND ART

*Dendrobium* is one of the largest genera of Orchidaceae, with more than 1500 species in the world, widely distributed in tropical and subtropical regions such as Asia, Europe and Oceania. There are about 76 species of *Dendrobium* in China, which is mainly distributed in Southwest, East and South China. *Dendrobium* has the functions of nourishing yin and clearing heat, benefiting the stomach and promoting fluid production, moistening lung to arrest cough, and it is often used to treat various diseases such as low fluid due to fever, dry mouth and excessive thirst, and asthenic heat after illness. Modern pharmacological studies have shown that the main functional components of *Dendrobium* are water-soluble polysaccharides. Water-soluble polysaccharides are able to significantly enhance immune responses and have effects of cancer prevention, anticancer, antiaging, antioxidation and antiradiation, and are widely used in drugs, functional foods and cosmetics.

At present, greenhouse planting is the most widely used artificial planting method of *Dendrobium candidum*. When artificially planting *Dendrobium*, it should be planted in a place where the climate and environment are close to the growth requirements of *Dendrobium candidum*. Sawdust, bark and hemp are used as the planting medium. Moisture, temperature and light are intelligently controlled. Compared with wild *Dendrobium candidum*, *Dendrobium candidum* planted in greenhouse grows better, with thicker and stronger branches and higher yields. However, the drought and cold resistance of *Dendrobium candidum* planted in greenhouse are poor, and the accumulation of metabolites in *Dendrobium candidum* is low, resulting in the unsatisfactory content of polysaccharides and alkaloids in *Dendrobium candidum* planted in greenhouse. Therefore, the quality of *Dendrobium candidum* grown in greenhouses is quite different from that of wild *Dendrobium candidum*. It is urgent to adjust the planting methods of *Dendrobium candidum* to improve the quality of artificially planted *Dendrobium candidum* to meet the market demand.

SUMMARY

The present disclosure aims to provide a method for organically planting *Dendrobium* to solve the technical problem of unsatisfactory quality of artificially planted *Dendrobium candidum* in the prior art.

In order to achieve the above purpose, the present disclosure provides the following technical solution:

The present disclosure provides a method for organically planting *Dendrobium*, including an epiphytic planting step of *Dendrobium*: closing a root system of a seedling clump to a tree trunk by a non-woven fabric block, placing a planting medium between the non-woven fabric block and the tree trunk, and spraying nutrient solution outside the non-woven fabric block; wherein, raw materials of the planting medium include fermented powder of *Dendrobium candidum* leaves and sawdust; a method for preparing the fermented powder of *Dendrobium candidum* leaves is as follows: cutting *Dendrobium candidum* leaves into small pieces and mashing the small pieces of *Dendrobium candidum* leaves to obtain materials to be fermented, and then adding liquid medium to the materials to be fermented to obtain fermentation system, sterilizing the fermentation system, adding fermentation bacteria to the fermentation system to obtain a mixture, fermenting and filtering the mixture to obtain post-culturing fermentation broth and fermented product of *Dendrobium candidum* leaves, dewatering and crushing the fermented product of *Dendrobium candidum* leaves to obtain fermented powder of *Dendrobium candidum* leaves.

The principle and advantages of the technical solution of the present disclosure are:

With the rapid development of *Dendrobium candidum* planting industry, the biomimetic cultivation of *Dendrobium candidum* under the forest shows its advantages. The biomimetic cultivation of *Dendrobium candidum* under the forest imitates the wild growth environment, so that *Dendrobium candidum* has the characteristics of developed root system and irregular growth of stem, and the shape is close to that of wild *Dendrobium candidum*. In the present disclosure, an epiphytic planting method is used to simulate the wild environment. Compared with planting *Dendrobium candidum* in greenhouse, the method of the present disclosure may improve the content of alkaloids and polysaccharides in *Dendrobium candidum*, and then improve the quality of *Dendrobium candidum*.

In addition, in order to further promote the epiphytic growth of *Dendrobium candidum* on the trunk, a lot of research has been done on the epiphytic planting model. The inventors found that the recycling part of *Dendrobium* leaves discarded in the development of *Dendrobium* products may improve the quality of *Dendrobium*. The technical solution includes collecting discarded leaves and transforming the functional components in *Dendrobium* leaves through microbial fermentation. The fermented powder of *Dendrobium candidum* leaves transformed by microorganisms shows good growth promoting ability, which may significantly increase the content of polysaccharides in *Dendrobium* and improve the quality of *Dendrobium*. After analysis, it is found that, in the process of planting *Dendrobium* on the trunk, the rooting and epiphytic growth of *Dendrobium candidum* have a significant effect on the growth of *Dendrobium*. The fermented powder of *Dendrobium candidum* leaves in the present disclosure may play a positive role on the rooting and epiphytic growth of *Dendrobium candidum*, promote the planting of *Dendrobium candidum* on the trunk as soon as possible and adapt to growth environment, and create conditions for the subsequent synthesis and manufacture of polysaccharides and other substances. In addition, the planting medium also continuously provide nutrients during the growth process of *Dendrobium* after taking root and epiphytic, so as to improve the quality of *Dendrobium*.

In one embodiment, a ratio of the materials to be fermented and the liquid medium is 1 g: 20-40 mL.

In the present disclosure, the above amount of liquid medium provides sufficient space and nutrition for the growth of microorganisms, and the microorganisms may fully ferment the fermentation materials in the above liquid medium.

In one embodiment, a mass ratio of the fermented powder of *Dendrobium candidum* leaves and sawdust is 1:3-5.

In the present disclosure, the fermented powder of *Dendrobium candidum* leaves is dispersed with sawdust to form a planting medium. Under the above proportion, the fermented powder of *Dendrobium candidum* leaves may play an ideal role in promoting the epiphytic growth of *Dendrobium candidum*.

In one embodiment, the fermentation bacteria include *Saccharomyces cerevisiae, Bacillus megaterium* and *Bacillus polymyxa* with a mass ratio of 1-2:1-3:2-4.

In the present disclosure, *Saccharomyces cerevisiae, Bacillus megaterium* and *Bacillus polymyxa* may play an ideal synergistic effect under the above proportion. However, the efficacy of fermented product and fermentation broth of *Dendrobium candidum* leaves obtained by single strain fermentation is poor, thus affecting the quality of *Dendrobium candidum*.

In one embodiment, the liquid medium includes 1.50 g/L of yeast extract, 4.00 g/L of peptone, 2.50 g/L of diammonium hydrogen citrate and 2.00 g/L of dipotassium hydrogen phosphate.

In the present disclosure, the liquid medium may effectively promote the growth of *Saccharomyces cerevisiae, Bacillus megaterium* and *Bacillus polymyxa*, so as to fully ferment the leaves of *Dendrobium*, so that the components in the leaves of *Dendrobium* are converted, thereby forming the functional components that promote the epiphytic growth of *Dendrobium* on the trunk.

In one embodiment, conditions of the fermenting are as follows: temperature of 37° C., rotation speed of 120 rpm, and time of 72 h.

In the present disclosure, the above fermentation conditions may ensure the full fermentation of *Dendrobium* leaves and further promote the formation of functional components with growth promoting effect.

In one embodiment, a method for preparing the nutrient solution includes the following steps: filtering the post-culturing fermentation broth, collecting a liquid phase to obtain a nutrient solution precursor, and then diluting the nutrient solution precursor with water to obtain the nutrient solution; a volume ratio of the nutrient solution precursor and water is 1:3.

In the present disclosure, the post-culturing fermentation broth contains a large number of secondary metabolites of bacteria, which can promote the growth of *Dendrobium*. Firstly, the bacteria in the post-culturing fermentation broth are removed. After the fermentation process, the activity of the bacteria is poor, and the nutrient solution precursor contains a large number of secondary metabolites, which may be used for the planting and culture of *Dendrobium*. The nutrient solution precursor is diluted in a certain proportion to obtain the nutrient solution for spraying.

In one embodiment, an amount of the planting medium is 100 g for each seedling clump; an amount of the nutrient solution is 50 mL for each seedling clump.

In the present disclosure, the above amount of nutrient solution may infiltrate the dry planting medium, the functional components are dissolved from the fermented powder of *Dendrobium candidum* leaves after infiltration, and play its growth promoting effect. At the same time, the secondary metabolites in the nutrient solution also play the corresponding growth promoting effect.

In one embodiment, the method further includes steps of cultivation and management after the epiphytic planting, spraying microbial agent on the outside of the non-woven fabric block every two months, strains of the microbial agent include *Saccharomyces cerevisiae, Bacillus megaterium* and *Bacillus polymyxa*.

In the present disclosure, spraying microbial agents every two months may maintain the flora balance of growth environment of *Dendrobium*, promote its growth and produce a large number of components with medicinal functions such as polysaccharides.

In one embodiment, mass percentage of the strains of the microbial agent accounts for 1-3% of the mass of the microbial agent.

In the present disclosure, the microbial agent containing the above mass percentage of bacteria may effectively promote growth.

DETAILED DESCRIPTION OF THE EMBODIMENTS

The following is further described in detail through specific examples:

Example 1

(1) Preparation Before Planting:

The evergreen broad-leaved forest with altitude of 800-1000 m, annual relative humidity of 60%-65% and average annual rainfall of 1100-1200 mm was selected for *Dendrobium candidum* planting. Trees with rough epidermis and above 15 cm in diameter at breast height were selected for epiphytic planting of *Dendrobium candidum*. The weeds under the trees were removed. Specifically, the weeds under the trees with the base of the trees as the center and a radius of 2 m were removed. The annual seedlings of *Dendrobium candidum* with normal root growth and no diseases and pests were selected for the experiment. The seedlings were separated to form small clusters, each of which contained 2-3 stems. The small clusters of seedlings shall be epiphytic planted within 3-4 days after preparing the seedlings.

(2) Epiphytic Planting of *Dendrobium*

Epiphytic planting of *Dendrobium* was carried out in mid March. The non-woven fabric was cut into 20×10 cm non-woven fabric block, the lower two corners and the upper one corner of the non-woven fabric block were fixed on the tree trunk by using a nail gun (the long sides of the non-woven fabric block were set horizontally), and then the lower part of the seedling clump was put into the pocket space formed by the non-woven fabric block and the tree trunk, then the planting medium was put into the space (the two corners at the lower end of the non-woven fabric block were tightened to ensure that the planting medium would not slip from below, or an additional fixing nail could also be inserted at the long side below the non-woven fabric block). Then the unfixed corner of the non-woven fabric block was fixed on the tree trunk by using the nail gun, so that the root system of the seedling clump was close to the tree trunk, so as to ensure that *Dendrobium candidum* was epiphytically planted, and further ensure that *Dendrobium candidum* would not slide from the space between the non-woven fabric block and the tree trunk. About 100 g of planting medium was used for each seedling clump, and after planting, nutrient solution was sprayed on the outside of non-woven fabric block, and 50 mL nutrient solution was used for each seedling clump. The horizontal spacing between adjacent non-woven fabric block was kept at more than 3 cm, and the planting of seedling clumps was started at the position of the trunk more than 50 cm above the ground, and the planting height of seedling clumps was not more than 2.5 m.

The raw materials of the planting medium included fermented powder of *Dendrobium candidum* leaves and sawdust with a mass ratio of 1:3-5. The ratio of 1:3 was used in this example. The method for preparing the fermented powder of *Dendrobium candidum* leaves was as follow: the discarded *Dendrobium candidum* leaves were cut into small pieces. The small pieces *Dendrobium candidum* leaves were mashed to obtain the materials to be fermented, and then the materials to be fermented were put into the liquid medium in the ratio of 1 g:20-40 mL (40 mL was selected in this example) to obtain the fermentation system. The method for preparing the liquid medium was as follows: various raw material components were added to water, the raw material components included yeast extract, peptone, diammonium hydrogen citrate and dipotassium hydrogen phosphate. The concentrations of yeast extract, peptone, diammonium hydrogen citrate and dipotassium hydrogen phosphate in the liquid medium were 1.50 g/L, 4.00 g/L, 2.50 g/L and 2.00 g/L respectively. The fermentation system was sterilized with moist heat at 121° C. and 0.1 MPa for 30 min. The fermentation bacteria was inoculated in the fermentation system according to the inoculation amount of 3-5% (mass percentage) (in this example, the inoculation amount was 5%, and the fermentation bacteria were fresh bacteria obtained through conventional activation culture in the prior art) after the fermentation system cool down, and then the fermentation bacteria was placed in a constant temperature shaking table at 37° C. and 120 rpm for 72 h. Fermentation microbes included *Saccharomyces cerevisiae* (ATCC 18824), *Bacillus megaterium* (ATCC 14581) and *Bacillus polymyxa* (ATCC 842) in the mass ratio of 1-2:1-3:2-4 (the mass ratio used in this example was 1:1:2). The solid-liquid separation was carried out by filtration to obtain the post-culturing fermentation broth and the fermented products of *Dendrobium candidum* leaves after the culture. The fermented products of *Dendrobium candidum* leaves were dried in an oven at 40° C. to constant weight after the fermentation products of *Dendrobium candidum* leaves were washed with clean water, and then the dried fermentation products of *Dendrobium candidum* leaves were crushed (fermented powder of *Dendrobium candidum* leaves) and mixed with sawdust. The post-culturing fermentation broth was filtered to collect the liquid phase (The post-culturing fermentation broth was centrifuged before filtration to make the bacteria settle). The post-culturing fermentation broth was diluted with water to obtain the nutrient solution. 1 L of the post-culturing fermentation broth was diluted with 3 L of water. The nutrient solution was refrigerated at 4° C. before use. The nutrient solution was taken out and bathed in 37° C. water for 30 min before spraying. The nutrient solution could also be directly placed in the normal temperature environment until its temperature was consistent with the external temperature.

(3) Post Cultivation Management

In spring and winter, *Dendrobium* was sprayed with water mist every two days, by using the atomizing nozzles of the automatic water spray system for 30 minutes each time; In summer and autumn, *Dendrobium* was sprayed with water mist once in the morning and once in the evening for 30 minutes each time. The branches and leaves of the trees were properly trimmed, so that *Dendrobium candidum* received light with a light intensity of about 3500 lx. The temperature under the tree was kept at 20-25° C. in summer.

One month after planting, 50 mL of microbial agent was sprayed on the outside of the non-woven fabric block each day for 10 days. The method for preparing microbial agent was as follows: fermentation bacteria with mass percentage of 1-3% (3% mass percentage was used in this example) were added into the liquid medium. The fermentation bacteria included *Saccharomyces cerevisiae* (ATCC 18824), *Bacillus megaterium* (ATCC 14581) and *Bacillus polymyxa* (ATCC 842) with a mass ratio of 1-2:1-3:2-4 (the specific proportion used in this example was 1:1:2). The culture solution was the same as fermentation solution, but the microbial agent was not subjected to fermentation. In July of the next year, *Dendrobium candidum* was collected for detection. Each cluster of *Dendrobium candidum* was counted as a sample, and the stem near the root was collected to detect.

Example 2

This example was basically the same as Example 1, except that the preparation methods of planting medium and microbial agent were different, specifically as follows:

The raw materials of the planting medium included fermented powder of *Dendrobium candidum* leaves and sawdust with a mass ratio of 1:5. The method for preparing the fermented powder of *Dendrobium candidum* leaves was as follow: the discarded *Dendrobium candidum* leaves were cut into small pieces. The small pieces *Dendrobium candidum* leaves were mashed to obtain the materials to be fermented, and then the materials to be fermented were put into the liquid medium in the ratio of 1 g:20 mL to obtain the fermentation system. The method for preparing the liquid medium was as follows: various raw material components were added to water, the raw material components included yeast extract, peptone, diammonium hydrogen citrate and dipotassium hydrogen phosphate. The concentrations of yeast extract, peptone, diammonium hydrogen citrate and dipotassium hydrogen phosphate in the liquid medium were 1.50 g/L, 4.00 g/L, 2.50 g/L and 2.00 g/L respectively. The fermentation system was sterilized with moist heat at 121° C. and 0.1 MPa for 30 min. The fermentation bacteria was inoculated in the fermentation system according to the inoculation amount of 3% (mass percentage) after the fermentation system cool down, and then the fermentation bacteria was placed in a constant temperature shaking table at 37° C. and 120 rpm for 72 h. Fermentation bacteria included *Saccharomyces cerevisiae* (ATCC 18824), *Bacillus megaterium* (ATCC 14581) and *Bacillus polymyxa* (ATCC 842) in the mass ratio of 2:3:4. The solid-liquid separation was carried out by filtration to obtain the post-culturing fermentation broth and the fermented products of *Dendrobium candidum* leaves after the culture. The fermented products of *Dendrobium candidum* leaves were dried in an oven at 40° C. to constant weight after the fermentation products of *Dendrobium candidum* leaves were washed with clean water, and then the dried fermentation products of *Dendrobium candidum* leaves were crushed (fermented powder of *Dendrobium candidum* leaves) and mixed with sawdust. The post-culturing fermentation broth was filtered to collect the liquid phase (The post-culturing fermentation broth was centrifuged before filtration to make the bacteria settle). The post-culturing fermentation broth was diluted with water to obtain the nutrient solution. 1 L of the post-culturing fermentation broth was diluted with 3 L of water. The nutrient solution was refrigerated at 4° C. before use.

The method for preparing microbial agent was as follows: fermentation bacteria with mass percentage of 1% were added into the liquid medium. The fermentation bacteria included *Saccharomyces cerevisiae* (ATCC 18824), *Bacillus megaterium* (ATCC 14581) and *Bacillus polymyxa* (ATCC 842) with a mass ratio of 2:3:4. The culture solution was the same as fermentation solution, but the microbial agent was not subjected to fermentation. In July of the next year, *Dendrobium candidum* was collected for detection. Each cluster of *Dendrobium candidum* was counted as a sample, and the stem near the root was collected to detect.

Comparison 1

The comparison was basically the same as that of Example 1. The difference from Example 1 was that the planting medium was not used and the nutrient solution was not sprayed during epiphytic planting.

Comparison 2

The comparison was basically the same as that of Example 1. The difference from Example 1 was that microbial agents were not sprayed in post cultivation management.

Comparison 3

The comparison was basically the same as that of Example 1. The difference from Example 1 was that the method for preparing the fermented product of *Dendrobium candidum* leaves and the post-culturing fermentation broth, the method included the following steps:

The method for preparing the fermented product of *Dendrobium candidum* leaves was as follow: the discarded *Dendrobium candidum* leaves were cut into small pieces. The small pieces *Dendrobium candidum* leaves were mashed to obtain the materials to be fermented, and then the materials to be fermented were put into the liquid medium in the ratio of 1 g:40 mL to obtain the fermentation system. The method for preparing the liquid medium was as follows: various raw material components were added to water, the raw material components included yeast extract, peptone, diammonium hydrogen citrate and dipotassium hydrogen phosphate. The concentrations of yeast extract, peptone, diammonium hydrogen citrate and dipotassium hydrogen phosphate in the liquid medium were 1.50 g/L, 4.00 g/L, 2.50 g/L and 2.00 g/L respectively. The fermentation system was sterilized with moist heat at 121° C. and 0.1 MPa for 30 min. The fermentation bacteria was inoculated in the fermentation system according to the inoculation amount of 5% (mass percentage) after the fermentation system cool down, and then the fermentation bacteria was placed in a constant temperature shaking table at 37° C. and 120 rpm for 72 h. Fermentation bacteria were *Saccharomyces cerevisiae* (ATCC 18824). The solid-liquid separation was carried out by filtration to obtain the post-culturing fermentation broth and the fermented products of *Dendrobium candidum* leaves after the culture.

Comparison 4

The comparison was basically the same as that of Comparison 3. The difference from Comparison 3 was that *Bacillus megaterium* was used instead of *Saccharomyces cerevisiae*.

Comparison 5

The comparison was basically the same as that of Comparison 3. The difference from Comparison 3 was that *Bacillus polymyxa* was used instead of *Saccharomyces cerevisiae*.

Comparison 6

The comparison was basically the same as that of Example 1. The difference from Example 1 was that the method for preparing planting medium: leaves of *Dendrobium candidum* were dried at 50° C. to constant weight, crushed and mixed with sawdust to obtain planting medium. The mass ratio of dried *Dendrobium candidum* leaves to sawdust was 1:3. In addition, during epiphytic planting, the nutrient solution sprayed was the microbial inoculum in Example 1.

Experimental Example 1: Study on the Quality of *Dendrobium candidum*

In this Experimental Example, the content of polysaccharide in *Dendrobium candidum* planted by the method of Examples 1 and 2 and Comparisons 1-6 were detected. The method for extracting polysaccharide of *Dendrobium* was as follows: 100 g of fresh *Dendrobium candidum* in Examples 1 and 2 and Comparisons 1-6 were weighed (The method for sampling see Example 1) and put in an oven at 120° C. for 30 minutes. Then the temperature of the oven was adjusted to 45° C. to dry *Dendrobium candidum* to constant weight to obtain the dried *Dendrobium candidum*. The dried *Dendrobium candidum* was crushed and passed through 60 meshes to obtain the sample to be extracted. 10 g of sample to be extracted was taken and soaked in 80 mL of petroleum ether at 80° C. for 2 h, and the resulting soaked mixture was filtered to take the solid phase. Then, the solid phase was soaked in 80 mL of ethanol with 80% vol/vol at 80° C. for 2 h, and the obtained soaked mixture was filtered to take the solid phase. Finally, the solid phase was soaked in 50 mL of water at 90° C. for 3 h, repeated once, and the filtrate was combined to obtain the substance to be tested.

The content of polysaccharide in *Dendrobium candidum* was determined by phenol sulfuric acid method. The specific test steps were as follows: first, the standard curve was drawn using glucose standard. 150 mg of dry constant weight glucose was accurately weighed, and put into a 500 mL volumetric flask. Distilled water was added to dissolve and fix the volume; 0.00, 0.20, 0.30, 0.40, 0.50, 0.60 and 0.70 mL of above prepared glucose solution was accurately sucked and placed into a plug test tube; distilled water was added to make the volume of 2 mL, then 1 mL of 5% phenol solution was added. 5 mL of concentrated sulfuric acid was quickly added after shaking well to obtain a mixture. The mixture was shaken well and placed for 5 min; The mixture after being placed was placed in 90° C. water bath for 15 min, cooled at room temperature. The absorbance of the cooled mixture was measured at the wavelength of 490 nm. The standard curve was drawn. The substance to be tested was determined by phenol-sulfate acid method (diluted according to the actual situation), and the absorbance was measured at the wavelength of 490 nm. The content of polysaccharide in *Dendrobium candidum* sample (calculated by dry weight) was calculated from the standard curve and converted into the form of mass percentage (%). 6 samples of *Dendrobium candidum* from each example or comparison were taken for testing, and the experimental results were shown in table 1.

TABLE 1 content of polysaccharide in *Dendrobium candidum*
obtained by different planting methods

| Groups | Content of Polysaccharide in *Dendrobium candidum* (%) | | | | | | |
|---|---|---|---|---|---|---|---|
| | Sample 1 | Sample 2 | Sample 3 | Sample 4 | Sample 5 | Sample 6 | Mean value ± standard deviation |
| Example 1 | 36.1 | 37.2 | 36.2 | 39.2 | 38.3 | 36.7 | 37.28 ± 1.24 |
| Example 2 | 37.5 | 36.1 | 35.9 | 39.9 | 36.7 | 38.8 | 37.48 ± 1.59 |
| Comparison 1 | 32.1 | 35.4 | 30.7 | 33.2 | 30.9 | 29.5 | 31.97 ± 2.10 |
| Comparison 2 | 34.2 | 33.6 | 31.8 | 33.4 | 35.8 | 35.7 | 34.08 ± 1.51 |
| Comparison 3 | 34.9 | 33.5 | 31.6 | 34.3 | 32.5 | 31.5 | 33.05 ± 1.41 |
| Comparison 4 | 30.6 | 33.7 | 35.6 | 32.8 | 33.1 | 33.7 | 33.25 ± 1.62 |
| Comparison 5 | 34.8 | 33.6 | 34.6 | 30.5 | 33.6 | 34.9 | 33.67 ± 1.66 |
| Comparison 6 | 33.3 | 31.6 | 30.5 | 34.3 | 31.5 | 32.7 | 32.32 ± 1.38 |

According to Table 1, in Examples 1 and 2, the content of polysaccharide in *Dendrobium candidum* is more than 37%. The planting method of the present disclosure improves the quality of *Dendrobium candidum*. The content of polysaccharides in *Dendrobium* in Comparisons 1-6 is significantly different from that in Example 1 and Example 2 (t-test, $P<0.05$). For Comparison 1, when epiphytic planting is carried out, the planting medium is not used and nutrient solution is not sprayed, resulting in the decrease of content of polysaccharide in *Dendrobium candidum*. For Comparison 2, the quality of *Dendrobium candidum* is also negatively affected by not spraying microbial agents in post cultivation management. However, the content of polysaccharide in *Dendrobium candidum* obtained in Comparison 2 is slightly higher than that in other Comparisons, which shows that the planting medium of the present disclosure plays an important role in the initial stage of epiphytic growth of *Dendrobium candidum*. If the planting medium is not used, the rooting and epiphytic condition of *Dendrobium candidum* on the surface of trunk is not ideal, which will affect the subsequent growth process. The method for preparing the post-culturing fermentation broth and the fermented products of *Dendrobium candidum* leaves after the culture in Comparison 3 is changed, and only *Saccharomyces cerevisiae* is used in fermentation. For Comparison 4, only *Bacillus megaterium* is used in fermentation, and for Comparison 5, only *Bacillus polymyxa* is used in fermentation. A single strain is used for fermentation in Comparisons 3-5, and the obtained fermented products of *Dendrobium candidum* leaves and the post-culturing fermentation broth have poor efficacy, which affects the quality of *Dendrobium candidum*. In Comparison 6, when the planting medium is prepared, the leaves of *Dendrobium candidum* are not fermented, so the planting medium of Comparison 6 dose not promote the growth of *Dendrobium candidum* satisfactorily.

The above is merely the examples of the present disclosure. Common knowledge such as well-known specific technical solutions and/or characteristics in the solutions are not described too much here. It should be pointed out that for those skilled in the art, several modifications and improvements can be made without departing from the technical solution of the present disclosure, which should also be regarded as the protection scope of the present disclosure, and these will not affect the practicability of the present disclosure. The protection scope of the present disclosure shall be based on the content of the claims, and the specific embodiments and other records in the description can be used to explain the content of the claims.

What is claimed is:

1. A method for organically planting *Dendrobium*, comprising the following steps: 1) cutting *Dendrobium candidum* leaves into small pieces and mashing the small pieces of *Dendrobium candidum* leaves to obtain materials to be fermented, and then adding liquid medium to the materials to be fermented to obtain fermentation mixture, sterilizing the fermentation mixture, adding fermentation microbes to the fermentation mixture to obtain a mixture, fermenting, and filtering the mixture to obtain fermented products of *Dendrobium candidum* leaves, and drying and crushing the fermented products of *Dendrobium candidum* leaves to obtain fermented powder of *Dendrobium candidum* leaves; 2) mixing the fermented powder of *Dendrobium candidum* leaves and sawdust to obtain planting medium; and 3) wrapping a root system of a cluster of seedlings to a tree trunk with a non-woven fabric piece, placing the planting medium between the non-woven fabric piece and the tree trunk, and spraying nutrient solution on the outer surface of the non-woven fabric piece; and wherein the fermentation microbes comprise *Saccharomyces cerevisiae, Bacillus megaterium* and *Bacillus polymyxa* with the mass ratio of 1-2:1-3:2-4.

2. The method according to claim 1, wherein the ratio of the materials to be fermented to the liquid medium is 1 g: 20-40 mL.

3. The method according to claim 2, wherein the mass ratio of the fermented powder of *Dendrobium candidum* leaves to sawdust is 1:3-5.

4. The method according to claim 1, wherein the liquid medium comprises 1.50 g/L of yeast extract, 4.00 g/L of peptone, 2.50 g/L of diammonium hydrogen citrate and 2.00 g/L of dipotassium hydrogen phosphate.

5. The method according to claim 4, wherein conditions of the fermenting step are as follows: temperature of 37° C., rotation speed of 120 rpm, and time of 72 h.

6. The method according to claim 5, wherein the nutrient solution is prepared by the following steps: filtering the post-culturing fermentation broth, collecting the liquid phase to obtain a nutrient solution precursor, and then diluting the nutrient solution precursor with water to obtain the nutrient solution; and the volume ratio of the nutrient solution precursor to water is 1:3.

7. The method according to claim 6, wherein the amount of the planting medium is 100 g for each seedling clump; and the amount of the nutrient solution is 50 mL for each seedling clump.

8. The method according to claim 7, further comprising the steps of spraying microbial agent on the outer surface of the non-woven fabric piece every two months, wherein the microbial agent comprises fermentation microbes, and the fermentation microbes comprise strains of the combination of *Saccharomyces cerevisiae, Bacillus megaterium* and *Bacillus polymyxa*.

9. The method according to claim 8, wherein the mass percentage of the strains of the microbial agent accounts for 1-3% of the mass of the microbial agent.

* * * * *